United States Patent
Flügel et al.

(10) Patent No.: US 12,031,991 B2
(45) Date of Patent: *Jul. 9, 2024

(54) IN VITRO METHOD FOR DETECTING INTESTINAL BARRIER FAILURE IN ANIMALS

(71) Applicant: EVONIK OPERATIONS GMBH, Essen (DE)

(72) Inventors: Monika Flügel, Steinhagen (DE); Stefan Pelzer, Gütersloh (DE); Frank Thiemann, Nottuln (DE); Filip Van Immerseel, Eke (BE); Richard Ducatelle, Wortegem-Petegem (BE); Evy Goossens, Wachtebeke (BE); Bart Devreese, Vosselare (BE); Griet Debyser, Bruges (BE)

(73) Assignee: Evonik Operations GmbH, Essen (DE)

( * ) Notice: Subject to any disclaimer, the term of this patent is extended or adjusted under 35 U.S.C. 154(b) by 634 days.

This patent is subject to a terminal disclaimer.

(21) Appl. No.: 16/977,003

(22) PCT Filed: Feb. 28, 2019

(86) PCT No.: PCT/EP2019/054939
§ 371 (c)(1),
(2) Date: Aug. 31, 2020

(87) PCT Pub. No.: WO2019/166531
PCT Pub. Date: Sep. 6, 2019

(65) Prior Publication Data
US 2021/0003592 A1 Jan. 7, 2021

(30) Foreign Application Priority Data

Mar. 2, 2018 (EP) .................................. 18159632

(51) Int. Cl.
*G01N 33/68* (2006.01)
*G01N 33/543* (2006.01)

(52) U.S. Cl.
CPC ....... *G01N 33/6893* (2013.01); *G01N 33/543* (2013.01); *G01N 33/54306* (2013.01); *G01N 33/54388* (2021.08); *G01N 2333/79* (2013.01); *G01N 2800/06* (2013.01)

(58) Field of Classification Search
CPC ............. G01N 33/6893; G01N 33/543; G01N 33/54306; G01N 33/54388; G01N 2333/79; G01N 2800/06; G01N 33/53; G01N 33/68; Y02A 40/70
USPC .......................................................... 435/7
See application file for complete search history.

(56) References Cited

U.S. PATENT DOCUMENTS

| | | | |
|---|---|---|---|
| 5,094,956 A * | 3/1992 | Grow .................. | G01N 33/528 436/66 |
| 5,538,851 A | 7/1996 | Fach et al. | |
| 5,874,220 A | 2/1999 | Fach et al. | |
| 6,812,023 B1 | 11/2004 | Lamparski et al. | |
| 6,899,863 B1 | 5/2005 | Dhellin et al. | |
| 7,198,923 B1 | 4/2007 | Abrignani et al. | |
| 7,374,927 B2 | 5/2008 | Palma et al. | |
| 8,263,088 B2 | 9/2012 | Moore et al. | |
| 8,673,560 B2 | 3/2014 | Leamon et al. | |
| 11,643,696 B2 | 5/2023 | Flügel et al. | |
| 2002/0048576 A1* | 4/2002 | Anderson ............... | A61P 31/04 424/94.63 |
| 2003/0050470 A1 | 3/2003 | An et al. | |
| 2004/0101860 A1 | 5/2004 | Jones et al. | |
| 2007/0042354 A1 | 2/2007 | Engelhard et al. | |
| 2010/0291131 A1 | 11/2010 | Moore et al. | |
| 2011/0117540 A1* | 5/2011 | Cary .................... | G01N 33/558 435/5 |
| 2012/0058904 A1 | 3/2012 | Shanks et al. | |
| 2014/0099373 A1 | 4/2014 | Broomhead et al. | |
| 2014/0178885 A1 | 6/2014 | Park et al. | |
| 2016/0040119 A1* | 2/2016 | Hashman ................ | C12N 1/20 424/93.46 |

(Continued)

FOREIGN PATENT DOCUMENTS

CN 102697812 10/2012
CN 104531867 4/2015

(Continued)

OTHER PUBLICATIONS

Xie, H., Huff, G. R., Huff, W. E., Balog, J. M., Holt, P., & Rath, N. C. Identification of ovotransferrin as an acute phase protein in chickens.(2002). Poultry Science, 81(1), 112-120. (Year: 2002).*
Sheng, J. Q., Li, S. R., Wu, Z. T., Xia, C. H., Wu, X., Chen, J., & Rao, J.(2009). Transferrin dipstick as a potential novel test for colon cancer screening:a comparative study with immuno fecal occult blood test. Cancer epidemiology, biomarkers & prevention, 18(8), 2182-2185 (Year: 2009).*
Rath, N. C., Anthony, N. B., Kannan, L., Huff, W. E., Huff, G. R., Chapman, H. D., Erf, G. F., & Wakenell, P. (2009). Serum ovotransferrin as a biomarker of inflammatory diseases in chickens. Poultry science, 88(10), 2069-2074. (Year: 2009).*

(Continued)

*Primary Examiner* — Ann Montgomery
*Assistant Examiner* — Chau N. B. Tran
(74) *Attorney, Agent, or Firm* — Law Office of: Michael A. Sanzo, LLC

(57) ABSTRACT

The present invention pertains to an in vitro method for detecting intestinal barrier failure in an avian population, the method comprising the following steps: a) collecting a pooled fecal sample deriving from an avian population and b) determining the amount of at least one protein marker contained in said sample; wherein the at least one protein marker comprises or consists of an acute phase protein or a functional fragment thereof, and wherein an increased amount of said at least one protein marker contained in said sample versus a reference sample indicates intestinal barrier failure.

17 Claims, No Drawings

(56) References Cited

U.S. PATENT DOCUMENTS

| | | |
|---|---|---|
| 2016/0041153 A1 | 2/2016 | Brown et al. |
| 2017/0108503 A1 | 4/2017 | Klass et al. |
| 2018/0312905 A1 | 11/2018 | Igwe |
| 2020/0239938 A1 | 7/2020 | Kappel et al. |
| 2021/0011027 A1 | 1/2021 | Flügel et al. |
| 2021/0139955 A1 | 5/2021 | Flügel et al. |
| 2021/0207193 A1 | 7/2021 | Thiemann et al. |
| 2021/0262031 A1 | 8/2021 | Igwe et al. |
| 2022/0050115 A1 | 2/2022 | Pelzer et al. |
| 2022/0259642 A1 | 8/2022 | Dargatz et al. |
| 2023/0066330 A1 | 3/2023 | Raddatz et al. |

FOREIGN PATENT DOCUMENTS

| | | | |
|---|---|---|---|
| CN | 107090518 | | 8/2017 |
| EP | 0 281 251 | | 9/1988 |
| EP | 2 495 025 | A1 | 9/2012 |
| EP | 2 740 536 | A2 | 6/2014 |
| JP | 2015-039320 | | 3/2015 |
| KR | 2008-0082370 | | 9/2008 |
| RU | 2472162 | | 1/2013 |
| WO | WO 2005/016962 | | 2/2005 |
| WO | WO 2005/122790 | | 12/2005 |
| WO | WO 2008/148166 | | 12/2008 |
| WO | WO 2012/017466 | | 2/2012 |
| WO | WO 2014/012168 | | 1/2014 |
| WO | WO 2014/107571 | | 7/2014 |
| WO | WO 2015/103710 | | 7/2015 |
| WO | WO 2016/011258 | | 1/2016 |
| WO | WO-2016142146 | A2 * | 9/2016 ............... A61P 1/00 |
| WO | WO 2016/201272 | | 12/2016 |
| WO | WO 2018/206690 | | 11/2018 |
| WO | WO 2019/166534 | | 9/2019 |
| WO | WO 2019/238561 | | 12/2019 |

OTHER PUBLICATIONS

O'reilly, E. L., & Eckersall, P. D. (2014). Acute phase proteins: a review of their function, behaviour and measurement in chickens. World's Poultry Science Journal, 70(1), 27-44. (Year: 2014).*

Barrett, A. J., & McDonald, J. K. (1986). Nomenclature: protease, proteinase and peptidase. The Biochemical journal, 237(3), 935. (Year: 1986).*

Walker et al (Fecal lactoferrin is a sensitive and specific marker of disease activity in children and young adults with inflammatory bowel disease, J Pediatr Gastroenterol Nutr. Apr. 2007;44(4):414-22) (Year: 2007).*

Cackle Hatchery (Coccidiosis: the signs, symptoms and treatment, 2015). (Year: 2015).*

Genbank Accession No. EU143239—Clostridium perfringens necrotic enteritis toxin B precursor (netB) gene, complete cds (submitted Sep. 7, 2007, retrieved May 12, 2021 from https://www.ncbi.nlm.nih.gov/nuccore/EU143239).

Genbank Accession No. JF298802—Clostridium perfringens strain CPB228 alpha toxin gene, partial cds (submitted Jan. 30, 2011, retrieved May 13, 2021 from https://www.ncbi.nlm.nih.gov/nuccore/JF298802).

Genbank Accession No. EU839779—Clostridium perfringens strain S01 phospholipase C (plc) gene, complete cds (submitted Jun. 20, 2008, retrieved May 13, 2021 from https://www.ncbi.nlm.nih.gov/nuccore/EU839779).

Abilgaard, et al., "Sequence variation in the α-toxin encoding plc gene of Clostridium perfringens strains isolated from diseased and healthy chickens," Veterinary Microbiology 136(3-4):293-299 (May 2009).

Albini, et al., "Real-time multiplex PCR assays for reliable detection of Clostridium perfringens toxin genes in animal isolates," Veterinary Microbiology 127*(1-2):179-185 (Feb. 2008).

Farzan, et al., "An investigation into the association between cpb2-encoding Clostridium perfringens type A and diarrhea in neonatal piglets," *Canadian Journal of Veterinary Research 77*(1):45-53 (Jan. 2013).

Llanco, et al., "Toxinotyping and antimicrobial susceptibility of Clostridium perfringens isolated from broiler chickens with necrotic enteritis," *International Journal of Microbiology Research 4*(7):290 (2012).

Mostafa, et al., "Research Article: Multiplex PCR and Detection of netB Gene of Clostridium perfringens from Broilers with Necrotic Enteritis," *Asian J. Anim. Vet. Adv. 11*: 248-252 (Mar. 2016).

Restriction Requirement for copending U.S. Appl. No. 16/612,398, dated May 18, 2021.

U.S. Appl. No. 17/627,399, filed Jan. 14, 2022, US-2022/0259642 A1, Aug. 18, 2022, Dargatz.

U.S. Appl. No. 17/794,269, filed Jul. 21, 2022, Raddatz.

Notice of Appeal filed Jan. 18, 2021, for copending U.S. Appl. No. 15/555,531.

Appeal Brief filed Apr. 19, 2021, for copending U.S. Appl. No. 15/555,531.

"Clostridium perfringens NetB DNA SEQ ID: 1", XP-002761707, Database accession No. AUJ86218 (Feb. 2009).

"Human PRO nucleotide sequence SEQ ID: 410", XP-002761706, Database accession No. AUZ24794 (Mar. 2009).

"Clostridium perfringens strain NE_10 plasmid pNetB-NE10, complete sequence," XP-002761708, Database accession No. JQ655731 (Dec. 2012).

Database WPI, Thomson Scientific, London, GB; XP-002744039; CN 102 697 812 A (Univ. Shandong Agric.), abstract (Oct. 2012).

Database accession No. BDE57256; *Clostridium perfrigens* netB gene specific forward PCR primer, (Nov. 2016).

Database accession No. EA946288; Sequence 166055 from U.S. Pat. No. 7,374,927; (Aug. 2008).

Database accession No. EA876028; Sequence 95795 from U.S. Pat. No. 7,374,927; (Aug. 2008).

Database accession No. BCL09680; Avena sativa BAD specific multiplex PCR primer; (Mar. 2016).

Database accession No. BCL16835; Avena sativa BAD specific multiplex PCR primer; (Mar. 2016).

Database accession No. HJ900945; Sequence 97404 from U.S. Pat. No. 8,673,560; (Feb. 2015).

Database accession No. AWZ90261; *Clostridium perfrigens* detecting PCR primer; (Jul. 2009).

Database accession No. AFB71766; *Campylobacter* sp. PCR primer; (May 2007).

Database accession No. HW832967; A method for simultaneous detection and/or quantification of multiple bacteria; (Oct. 2015).

Database accession No. GS_NUC_ALERT:WO2016201272.163953; standard, peptide; (Jun. 2015).

Aade, et al., "Haematological parameters change in *Gallus gallus domesticus* infected with cestode parasite," *International Multidisciplinary Research Journal 2*(4):13-15 (accepted Apr. 2012).

Allaart, et al., "NetB-producing and beta2-producing *Clostridium perfringes* associated with subclinical necrotic enteritis in laying hens in the Netherlands," *Avian Pathology 41*(6):541-546 (2012).

Benjamini, et al., "Controlling the False Discovery Rate: a Practical and Powerful Approach to Multiple Testing," *J.R. Statist. Soc. B. 57*(1):289-300.

Chen, et al., "Microfluidic isolation and transcriptome analysis of serum microvesicles," *Lab on a Chip 10*:505-511 (available online Dec. 2009).

Cheruvanky, et al., "Rapid isolation of urinary exosomal biomarkers using a nanomembrane ultrafiltration concentrator," *Am. J. Physiol. Renal Physiol. 292*(5):F1657-1661 (May 2007).

Chuka, et al., "A Comparison of the haematological and biochemical indices of broiler and red jungle (Hamburgh) fowl (*Gallus gallus domesticus*)," *Discovery Nature 1*(1):15-18 (Oct. 2012).

Clayton, et al., "Analysis of antigen presenting cell derived exosomes, based on immuno-magnetic isolation and flow cytometry," *J. Immunol. Methods 247*:163-174 (Jan. 2001).

Cooper, et al., "Diagnosing clostridial enteric disease in poultry," *Journal of Veterinary Diagnostic Investigation 25*(3):314-327 (2013).

Dinh, et al., "Modulation of microRNAs in two genetically disparate chicken lines showing different necrotic enteritis disease susceptibility," *Vet. Immunol. Immunopathol. 159*:74-82 (May 2014).

Garcia, et al., "Experimental infection of commercial layers using a *Salmonella enterica* serovar Gallinarum strain: Leukogram and

(56) References Cited

OTHER PUBLICATIONS serum acute-phase protein concentrations," *Brazillian Journal of Poultry Science* 11:263-270 (Oct.-Dec. 2009).
Gohari, et al., "A Novel Pore-Forming Toxin in Type A *Clostridium perfringens* Is Associated with Both Fatal Canine Hemorrhagic Gastroenteritis and Fatal Foal Necrotizing Enterocolitis," *PLoS One* 10(4):1-27 (Apr. 2015).
Goossens, et al., "*Clostridium perfringens* strains from bovine enterotoxemia cases are not superior in in vitro production of alpha toxin, perfringolysin O and proteolytic enzymes," *BMC Veterinary Research* 10(32):1-7 (2014).
Response to Restriction Requirement for copending U.S. Appl. No. 16/612,398, filed Jul. 17, 2021.
Abnous, et al., "Diets Enriched in Oat Bran or Wheat Bran Temporally and Differentially Alter the Composition of the Fecal Community of Rats," *The Journal of Nutrition* 139(11):2024-2031 (Sep. 2009).
Akbarmehr, "Isolation of *Salmonella* spp. from poultry (ostrich, pigeon and chicken) and detection of their hilA gene by PCR method," *African Journal of Microbiology Research* 4(24):2678-2681 (Dec. 2010).
Ammar, et al., "Virulence genotypes of clinical *Salmonella* Serovars from broilers in Egypt," *J. Infect. Dev. Ctries.* 10(4):337-346 (Apr. 2016).
Barwick, et al., "Prevalence of *Giardia* spp. and *Cryptosporidium* spp. on dairy farms in southeastern New York state," *Preventive Veterinary medicine* 59(1-2):1-11 (May 2003).
Black, et al., "Experimental *Campylobacter jejuni* Infection in Humans," *The Journal of Infectious Diseases* 157(3):472-479 (Mar. 1988).
Borges, et al., "Detection of virulence-associated genea in *Salmonella* Enteritidia iaolatea from chicken in South of Brazil," *Pesq. Vet. Bras.* 33(12):1416-1422 (Dec. 2013).
Brassard, et al., "Real-time PCR study of infection dynamics of Torque teno sus viruses in naturally infected pigs from nursery to slaughterhouse," *The Veterinary Journal* 197(2):506-508 (Aug. 2013).
Cardona-Castro, et al., "PCR test to detect hilA gene sequences of *Salmonella* spp in blood and feces samples," Abstracts of the General Meeting of the American Society for Microbiology, vol. 102, Section No. 237, Abstract C-267, p. 148 (May 2002).
Chandler-Bostock, et al., "Diversity of group A rotovirus on a UK pig farm," *Verteinary Microbiology* 180(3-4):205-211 (Nov. 2015).
Elder, et al., "Correlation of enterohemorrhagic *Escherichai coli* 0157 prevalence in feces, hides and carcasses of beef cattle during processing," *PNAS* 97(7):2999-3003 (Mar. 2000).
Fernandes Da Costa, et al., "Protection against avian necrotic entertitis after immunisation with NetB genetic or formaldhyde toxoids," *Vaccine* 31:4003-4008 (2013).
Guyard-nicodème, et al., "Effect of Feed Additives on Productivity and *Campylobacter* spp. Loads in Broilers Reared under Free Range Conditions," *Frontiers in Microbiology* 8(828):1-7 (May 2017).
Haas, et al., "A Quantitative Real-Time PCR Approach for Assessing *Campylobacter jejuni* and *Campylobacter coli* Colonization in Broiler Herds," *Journal of Food Protection* 80(4):604-608 (Apr. 2017).
Hofshagen, et al., "Toxin Production by Clostridium perfringens Isolated from Broiler Chickens and Capercaillies (*Tetrao urogallus*) with and without Necrotizing Enteritis," *Avian Diseases* 36(4):837-843 (Oct. 1992).
Hong, et al., "Rapid Detection of *Campylobacter coli, C. jejuni*, and *Salmonella enterica* on Poultry Carcasses by Using PCR-Enzyme-Linked Immunosorbent Assay," *Applied and Environmental Microbiology* 69(6):3492-3499 (Jun. 2003).
Kätterer, et al., "The impact of altered managment on long-term agriculture soil carbon stocks—a Swedish case study," *Nutrient Cycling in Agroecosystems* 70(2):179-187 (Oct. 2004).
Lee, et al., "Identification and cloning of two immunogenic *Clostridium perfringes* proteins, elongation factor Tu (EF-Tu) and pyruvate:ferredoxin oxidoreductase (PFO) of *C. perfringens*," *Research in Veterinary Science* 91(3)e80-e86 (Jan. 2011).
Lee, et al., "Immune and anti-oxidant effects of in ovo selenium proteinate on post-hatch experimental avian necrotic enteritis," *Veterinary Parasitology* 206(3):115-122 (Oct. 2014).
Miles, et al., "Spacial Contrasts of Seasonal and Intraflock Broiler Litter Trace Gas Emissions, Physical and Chemical Properties," *J. Environ. Qual.* 177(2):176-187 (Jan. 2011).
Musella, et al., "On the use of posterior predictive probabilities and prediction uncertainty to tailor informative sampling for parasitological surveillance in livestock," *Veterinary Parasitology* 205(1-2):158-168 (Sep. 2014).
Oosterom, et al., "Origin and Prevalence of *Campylobacter jejuni* in Poultry Processing," *Journal of Food Protection* 46(4):339-344 (Apr. 1983).
Pajaniappan, et al., "The *Campylobacter jejuni* cj0414 and cj0415 genes encode a gluconate dehydrogenase that is involved in chicken colonization," Abstract of the General Meeting of the American Society for Microbiology, vol. 105, p. 30 (2005); General Meeting of the American Society for Microbiology; Atlanta, Jun. 9, 2005).
Perko-mäkelä, et al., "Distribution of *Campylobacter jejuni* isolates from Turkey Farms and Different Stages at Slaughter Using Pulsed-Field Gel Electrophoresis and flaA-Short Variable Region," *Zoonoses Public Health* 58(6):388-398 (Sep. 2011).
Perko-mäkelä, et al., "A longitudinal study of *Campylobacter* distribution in a turkey production chain," *Acta Veterinaria Scandinavica* 51(18):1-10 (Apr. 2009).
Schallegger, et al., "Combined *Campylobacter jejuni* and *Campylobacter coli* Rapid Testing and Molecular Epidemiology in Conventional Broiler Flocks," *Zoonoses Public Health* 63(8):588-599 (Dec. 2016).
Schepers, et al., "Site-Specific Considerations for Managing Phosphorus," *J. Environ. Qual.* 29(1):125-130 (Jan. 2000).
Smith, et al., "Phenotypic and genotypic profiling of antimicrobial resistance in enteric *Escherichia coli* communities isolated from finisher pigs in Australia," *Australian Veterinary Journal* 94(10):371-376 (Oct. 2016).
Sun, et al., "Identification and molecular subtyping of *Campylobacter jejuni* isolated from chicken carcass," *Journal of Hygiene Research* 43(4):608-613 (Jul. 2014).
Van De Poel, et al., "Norwalk-Like Calicvirus Genes in Farm Animals," *Research* 6(1)36-41 (Jan.-Feb. 2000).
Wade, et al., "The true cost of necrotic enteritis," *World Poultry* 31:16-17 (2015).
Whittington, et al., "Use of Pooled Fecal Culture for Sensitive and Economic Detection of *Mycobacterium avium* subsp. *paratuberculosis* Infection in Flocks of Sheep," *Journal of Clinical Microbiology* 38(7):2550-2556 (Jul. 2000).
Williams, et al., "A new method for the experimental production of necrotic enteritis and its use for studies on the relationships between necrotic enteritis, coccidiosis and anticoccidial vaccination of chickens," *Parasitol Res.* 90:19-26 (2003).
Wu, et al., "Optimized Necrotic Enteritis Model Producing Clinical and Subclinical Infection of *Clostridium perfringens* in Broiler Chickens," *Avian Diseases* 54:1058-1065 (2010).
Wu, et al., "Two necrotic enteritis predisposing factors, dietary fishmeal and eimeria infection, induce large change in the caecal microbiota of broiler chickens," *Veterinary Microbiology* 169:188-197 (2014).
Xie, et al., "Prevalence of lapine rotavirus, astrovirus, and hepatitis E virus in Canadian domestic rabbit populations," *Veterinary Microbiology* 208:146-149 (Jul. 2017).
Zhu, et al., "Prevalence and quantification of *Campylobacter* contamination on raw chicken carcasses for retail in China," *Food Control* 75:196-202 (Dec. 2016).
U.S. Appl. No. 16/652,657, filed Mar. 31, 2020, US 2020/0239938 A1, Jul. 30, 2020, Kappel.
U.S. Appl. No. 17/059,431, filed Nov. 28, 2020, Thiemann.
U.S. Appl. No. 17/252,254, filed Dec. 14, 2020, Igwe.
Bailey, M., "The development and use of multiplex PCR protocols for the detection of *Clostridium perfringens* toxin encoding genes cpa, cpb, etx, ia, cpe, netB, and tpeL," Doctoral dissertation, Auburn University, (May 2013).

(56) References Cited

OTHER PUBLICATIONS

Merati, et al., "Identification and Characterization of *Clostridium perfringens* Isolated from Necrotic Enteritis in Broiler Chickens in Tiaret, Western Algeria," *Kafkas Univ Vet Fak Derg* 23(4)595-601 (Apr. 2017).

Nagpal, et al., Sensitive quantification of *Clostridium perfringens* in human feces by quantitative real-time PCR targeting alpha-toxin and enterotoxin genes, *BMC Microbiology* 15(1):1-12 (Oct. 2015).

Schlegel, et al., "Toxin-associated and other genes in *Clostridium perfringens* type A isolates from bovine clostridial abomasitis (BCA) and jejunal hemmorrhage syndrome (JHS)," *Canadian Journal of Veterinary Research* 76(4):248-254 (2012).

Singh, et al., "Molecular detection of *Clostridium perfringens* toxinotypes, Enteropathogenic *Escherichia coli*, rotavirus and coronavirus in diarrheic fecal samples of neonatal goat kids," *Veterinarski arhiv* 88(1):1-20 (2018).

Wu, et al., "Real-time PCR assay for *Clostridium perfringens* in broiler chickens in a challenge model of necrotic enteritis," *Applied and Environmental Microbiology* 77(3):1135-1139 (Feb. 2011).

Yadav, et al., "Molecular characterization and antimicrobial resistance profile of *Clostridium perfringens* type A isolates from humans, animals, fish and their environment," *Anaerobe* 47:120-124 (May 2017).

Yasugi, et al., "In vitro cytotoxicity induced by *Clostridium perfringens* isolate carrying a chromosomal cpe gene is exclusively dependent on sporulation and enterotoxin production," *Microbial Pathogenesis* 85:1-10 (Apr. 2015).

Non Final Office Action for copending U.S. Appl. No. 16/612,398, dated Feb. 15, 2022.

Yoo, et al., "Molecular Typing and Epidemiological Survey of Prevalence of *Clostridium perfringens* Types by Multiplex PCR," *Journal of Clinical Microbiology* 35(1):228-232 (Jan. 1997).

Rahman, et al., "Intestinal Hypoperfusion Contributes to Gut Barrier Failure in Severe Acute Pancreatitis," *J. Gastrointest. Surg.* 7(1):26-36 (2003).

Wu, et al., "Ovotransferrin: Structure, bioactivities and preparation," *Food Research International* 46(2):480-487 (2012).

Hacker, et al., "Pathogenicity islands of virulent bacteria: structure, function and impact on microbial evolution," *Molecular Microbiology* 23(6):1089-1097 (Mar. 1997).

Heikinheimo, et al., "Enumeration and Isolation of cpe-Positive *Clostridium perfringens* Spores from Feces," *Journal of Clinical Microbiology* 42(9):3992-3997 (Sep. 2004).

Jiang, et al., "Membrane vesicles of *Clostridium perfringens* type A strains induce innate and adaptive immunity," *International Journal of Medical Microbiology* 304:431-443 (May 2014).

Keyburn, et al., "Association between avian necrotic enteritis and *Clostridium perfringens* strains expressing NetB toxin," *Vet. Res.* 41:21 (accepted Nov. 2009).

Keyburn, et al., "NetB, a New Toxin That Is Associated with Avian Necrotic Enteritis Caused by *Clostridium perfringens*," *PLoS Pathogens* 4(2):e26 (Feb. 2008).

Kim, et al., "Noble Polymeric Surface Conjugated with Zwitterionic Moieties and Antibodies for the Isolation of Exosomes from human Serum," *Bioconjug. Chem.* 23:2114-2120 (Oct. 2012).

Koga, et al., "Exosome can prevent RNase from degrading microRNA in feces," *Journal of Gastrointestinal Oncology* 2(4):215-222 (Dec. 2011).

Kukier, et al., "Epidemiological Investigation of Animal Diseases Caused by *Clostridium perfringens* Strains Isolated From Feedingstuffs," *KRMIVA* 52:339-343 (Jan. 2010).

Leburn, et al., "Cattle enterotoxaemia and *Clostridium perfringens*: description, diagnosis and prophylaxis," *Veterinary Record* 167(1):13-22 (Jul. 2010).

Leep, et al., "Identification of Novel Pathogenicity Loci in *Clostridium perfringens* Strains That Cause Avian Necrotic Enteritis," *PLoS One* 5(5):e10795 (May 2010).

Li, et al., "Claudin-containing exosomes in the peripheral circulation of women with ovarian cancer," *BMC Cancer* 9:244 (Jul. 2009).

Li, et al., "Toxin Plasmids of *Clostridium perfringens*," *Microbiology and Molecular Biology Reviews* 77(2):208-233 (Jun. 2013).

Lovland, et al., "Diagnosing *Clostridium perfringes*-associated necrotic enteritis in broiler flocks by an immunoglobulin G anti-alpha-toxin enzyme-linked immunosorbent assay," *Avian Pathology* 32(5):527-534 (Oct. 2003).

Mathivanan, et al., "Proteomics Analysis of A33 Immunoaffinity-purfied Exosomes Released from the Human Colon Tumor Cell Line LIM1215 Reveals a Tissue-specific Protein Signature," *Mol. Cell. Proteomics* 9(2):197-208 (Feb. 2010).

McCourt, et al., "Sandwich ELISA detection of *Clostridium perfringens* cells and α-toxin from field cases of necrotic enteritis of poultry," *Veterinary Microbiology* 106:259-264 (2005).

Miranda, et al., "Nucleic acids within urinary exosomes/microvesicles are potential biomarkers for renal disease," *Kidney International* 78:191-199 (published online Apr. 2010).

Nakamura, et al., "Small cytoplasmic RNA (scRNA) gene from *Clostridium perfringens* can replace the gene for the *Bacillus subtilis* scRNA in both growth and sporulation," *Microbiology* 141:2965-2975 (1995).

Nilsson, et al., "Prostate cancer-derived urine exosomes: a novel approach to biomarkers for prostate cancer," *Br. J. Cancer* 100(10):1603-1607 (May 2009).

Obana, et al., "Structural Requirement in *Clostridium perfringens* Collagenase mRNA 5' Leader Sequence for Translation Induction through Small RNA-mRNA Base Pairing," *Journal of Bacteriology* 195(12):2937-2946 (Jun. 2013).
Ohtani, et al., "Identification of a novel locus that regulates expression of toxin genes in *Clostridium perfringens," FEMS Microbiology Letters 209*:113-118 (published online Mar. 2002).
Park, et al., "Characterization of *Clostridium perfrigens* isolates obtained from 2010 to 2012 from chickens with necrotic enteritis in Korea," *Poultry Science 94*(6):1158-1164 (Apr. 2015).
Pardon, et al., "Longitudinal study on morbidity and mortality in white veal calves in Belgium," *BMC Veterinary Research 8*(26):1-15 (2012).
Parreira, et al., "Sequence of Two Plasmids from *Clostridium perfringens* Chicken Necrotic Enteritis Isolates and Comparison with *C. perfringens* Conjugative Plasmids," *PLoS One 7*(11):e49753 (Nov. 2012).
Petit, et al., "*Clostridium perfringens*: toxinotype and genotype," *Trends in Microbiology 7*(3):104-110 (Mar. 1999).
Piercy, "Acute Phase Responses to Experimental Salmonellosis in Calves and Colibacillosis in Chickens: Serum Iron and Caeruloplasmin," *J. Comp. Path. 89*(3):309-319 (Jul. 1979).
Popoff, et al., "Genetic characteristics of toxigenic Clostridia and toxin gene evolution," *Toxicon 75*:63-89 (available online May 2013).
Popoff, et al., "Clostridial pore-forming toxins: Powerful virulence factors," *Anaerobe 30*:220-238 (available online Jun. 2014).
Rood, "Virulence Genes of *Clostridium perfringens," Annu. Rev. Microbiol. 52*:333-360 (1998).
Saita, et al., "Pathogenicity markers of *Clostridium* spp. in commercial turkeys," *Italian Journal of Animal Science 8*(4):781-784 (Jan. 2009).
Saleem, "Identification of biochemical markers for sub-clinical necrotic enteritis in broiler chickens" (In: Necrotic enteritis, disease induction, predisposing factors and novel biochemical markers in broiler chickens. Chapter 8, PhD thesis); University of Glasgow, UK (2013).
Schorey, et al., "Exosomes and other extracellular vesicles in host-pathogen interactions," *EMBO Reports 6*(1):24-43 (Jan. 2015).
Shao, et al., "Protein typing of circulating microvesicles allows real-time monitoring of glioblastoma therapy," *Nature Medicine 18*(12):1835-1840 (Dec. 2012).
Shojadoost, et al., "The successful experimental induction of necrotic enteritis in chickens by *Clostridium perfringes*: a critical review," *Veterinary Research 43*:74 (2012).
Skog, et al., "Glioblastoma microvesicles transport RNA and proteins that promote tumour growth and provide diagnostic biomarkers," *Nature Cell Biology 10*(12):1470-1476 (Jan.-Dec. 2008).
Staedel, et al., "MicroRNAs and bacterial infection," *Cellular Microbiology 15*(9):1496-1507 (Sep. 2013).

(56) References Cited

OTHER PUBLICATIONS

Taylor, et al., "MicroRNA signatures of tumor-derived exosomes as diagnostic biomarkers of ovarian cancer," *Gynecologic Oncology* 110(1):13-21 (Jul. 2008).
Thery, et al., "Isolation and Characterization of Exosomes from Cell Culture Supernatants and Biological Fluids," *Current Protocols in Cell Biology Chapter 3: Unit 3.22.1* (2006).
Titball, et al., "The *Clostridium perfringens* α-toxin," *Anaerobe* 5:51-64 (1999).
Wang, et al., "Integrated analysis of microRNA expression and mRNA transcriptome in lungs of avian influenza virus infected broilers," *BMC Genomics* 13:278 (2012).
Wei, et al., "Abundance of pathogens in the gut and litter of broiler chickens as affected by bacitracin and litter management," *Veterinary Microbiology* 166(3-4):595-601 (Oct. 2013).
Wise, et al., "Quantitive Detection of *Clostridium perfringensin* the Broiler Fowl Gastrointestinal Tract by Real-Time PCR," *Applied and Environmental Microbiology* 71(7):3911-3916 (Jul. 2005).
Wisnieswski, et al., "The Tcp conjugation system of *Clostridium perfringens,*" *Plasmid* 91:28-36 (May 2017).
Witwer, et al., "Standardization of sample collection, isolation and analysis methods in extracellular vesicle research," *Journal Extracellular Vesicles* 2:20360 (May 2013).
Wubbolts, et al., "Proteomic and Biochemical Analyses of Human B Cell-derived Exosomes," *J. Biol. Chem.* 278(13):10963-10972 (Mar. 2003).
Erol, et al., "Molecular typing of *Clostridium perfringens* isolated from turkey meat by multiplex PCR," *Letters in Applied Microbiology* 47(1):31-34 (2008).
Rood, et al., "Expansion of the *Clostridium perfringens* toxin-based typing scheme," *Anaerobe* 53:5-10 (2018).
Uzal, et al., "*Clostridium perfringens* type C and Clostridium difficile co-infection in foals," *Veterinary Microbiology* 156(3-4):395-402 (2012).
Amendment & Response filed May 16, 2022, for copending U.S. Appl. No. 16/612,398.
Non Final Office Action dated May 20, 2022, for copending U.S. Appl. No. 16/612,398.
International Search Report for corresponding PCT/EP2019/054939 Filed Feb. 28, 2019.
Written Opinion of the International Searching Authority for corresponding PCT/EP2019/054939 Filed Feb. 28, 2019.
International Preliminary Report on Patentability for corresponding PCT/EP2019/054939 Filed Feb. 28, 2019.
European Search Report and Search Opinion for EP 18159632 filed Mar. 2, 2018, for corresponding PCT/EP2019/054939 filed Feb. 28, 2019.
International Search Report for international application PCT/EP2019/054947 filed Feb. 28, 2019, corresponding to copending U.S. Appl. No. 16/977,023.
Written Opinion of the International Searching Authority for international application PCT/EP2019/054947 filed Feb. 28, 2019, corresponding to copending U.S. Appl. No. 16/977,023.
International Preliminary Report on Patentability for international application PCT/EP2019/054947 filed Feb. 28, 2019, corresponding to copending U.S. Appl. No. 16/977,023.
International Search Report for international application PCT/EP2018/062090 filed May 9, 2018, corresponding to copending U.S. Appl. No. 16/612,398.
Written Opinion of the International Searching Authority for international application PCT/EP2018/062090 filed May 9, 2018, corresponding to copending U.S. Appl. No. 16/612,398.
International Preliminary Report on Patentability for international application PCT/EP2018/062090 filed May 9, 2018, corresponding to copending U.S. Appl. No. 16/612,398.
Partial European Search Report for EP 17170811 filed May 12, 2017, for corresponding PCT/EP2018/062090 filed May 9, 2018.
European Search Report and Search Opinion for EP 19 20 9124 completed Mar. 3, 2020; (division of EP 17 17 0811 filed May 12, 2017).
International Search Report for international application PCT/EP2016/053502 filed Feb. 19, 2016, corresponding to copending U.S. Appl. No. 15/555,531.
Written Opinion of the International Searching Authority for international application PCT/EP2016/053502 filed Feb. 19, 2016, corresponding to copending U.S. Appl. No. 15/555,531.
International Preliminary Report on Patentability for international application PCT/EP2016/053502 filed Feb. 19, 2016, corresponding to copending U.S. Appl. No. 15/555,531.
Restriction Requirement dated Dec. 4, 2018 for copending U.S. Appl. No. 15/555,531.
Response to Restriction Requirement filed Feb. 4, 2019 for copending U.S. Appl. No. 15/555,531.
Amendment to Accompany Response to Restriction Requirement filed Feb. 4, 2019 for copending U.S. Appl. No. 15/555,531.
Non Final Office Action dated Feb. 21, 2019 for copending U.S. Appl. No. 15/555,531.
Amendment and Response to Non Final Office Action filed Jul. 22, 2019 for copending U.S. Appl. No. 15/555,531.
Final Office Action dated Oct. 9, 2019 for copending U.S. Appl. No. 15/555,531.
Amendment & Response to Accompany RCE filed Feb. 10, 2020 for copending U.S. Appl. No. 15/555,531.
Request for Continued Examination filed Feb. 10, 2020 for copending U.S. Appl. No. 15/555,531.
Non Final Office Action dated Apr. 6, 2020 for copending U.S. Appl. No. 15/555,531.
Response to Non Final Office Action filed Aug. 6, 2020 for copending U.S. Appl. No. 15/555,531.
Final Office Action dated Aug. 21, 2020 for copending U.S. Appl. No. 15/555,531.
Abeyrathne, et al., "Sequential separation of lysozyme, ovomucin, ovotransferrin, and ovalbumin from egg white," *Poultry Science* 93(4):1001-1009 (Mar. 2014).
Bischoff, et al., "Intestinal permeability—a new target for disease prevention and therapy," *BMC Gastroenterology* 14(1):189; pp. 1-25 (Nov. 2014).
Chapman, "Milestones in avian coccidiosis research: A review," *Poultry Science* 93:501-511 (2014).
Chen, et al., "Identification of potential biomarkers for gut barrier failure in broiler chickens," *Frontiers in Veterinary Science* 2:14; pp. 1-10 (May 2015).
Dalloul, et al., "Poultry coccidiosis: recent advancements in control measures and vaccine development," *Expert Rev. Vaccines* 5:143-163 (2006).
Ding, et al., "Transport of Antihypertensive Peptide RVPSL, Ovotransferrin 328-332, in Human Intestinal Caco-2 Cell Monolayers," *Journal of Agriculture and Food Chemistry* 63(37):8143-8150 (Sep. 2015).
Fukui, et al., "Changes of Intestinal Functions in Liver Cirrhosis," *Inflammatory Intestinal Diseases* 1(1):24-40 (Published online Mar. 2016).
Gholamiandehkordi, et al., "Quantification of gut lesions in a subclinical necrotic enteritis model," *Avian Pathology* 36(5):375-382 (Oct. 2007).
Gilani, et al., "New biomarkers for increased intestinal permeability induced by dextran sodium sulphate and fasting in chickens," *J Anim Physiol Anim Nutr* 101(5):e237-e245 (2017).
Goossens, et al., "Elevated faecal ovotransferrin concentrations are indicative for intestinal barrier failure in broiler chickens," *Vet Res* 49(1):1-8 (Jun. 2018).
Guerrant, et al., "Biomarkers of Environmental Enteropathy, Inflammation, Stunting and Impaired Growth in Children in Northeast Brazil," *PLoS One* 11(9):1-20 (Sep. 2016).
Johnson, et al., "Anticoccidial drugs: lesion scoring techniques in battery and floor-pen experiments with chickens," *Exp Parasitol* 28(1):30-36 (Aug. 1970).
Keyburn, et al., "Alpha-Toxin of *Clostridium perfringens* Is Not an Essential Virulence Factor in Necrotic Enteritis in Chickens," *Infection and Immunity* 74(11):6496-6500 (Nov. 2006).
Kogut, et al., "Editorial: Gut Health: The New Paradigm in Food Animal Production," *Frontiers in Veterinary Science* 3(71):1-4 (Aug. 2016).

(56) References Cited

OTHER PUBLICATIONS

Lee, et al., "Therapeutic potential of hen egg white peptides for the treatment of intestinal inflammation," *Journal of Functional Foods* 1(2):161-169 (Apr. 2009).

Moore, et al., "Necrotic enteritis predisposing factors in broiler chickens," *Avian Pathology* 45:275-281 (Accepted Jan. 2016).

M'Sadeq, et al., "Towards the control of necrotic enteritis in broiler chickens with in-feed antibiotics phasing-out worldwide," *Animal Nutrition* 1:1-11 (Available online Mar. 2015).

O'Reilly, et al., "Acute phase proteins: a review of their function, behaviour and measurement in chickens," *World Poultry Science Journal* 70(1):27-44 (Mar. 2014).

O'Reilly, Emily "Acute phase proteins and biomarkers for health in chickens," PhD thesis, University of Glasgow, Scotland, pp. 1-137 (Jan. 2016).

O'Reilly, Emily "Acute phase proteins and biomarkers for health in chickens," PhD thesis, University of Glasgow, Scotland, pp. 138-316 (Jan. 2016).

Pavia, et al., "Necrotic enteritis: Applications for the poultry industry," *Journal of Applied Poultry Research* 23:557-566 (2014).

Timbermont, et al., "Necrotic enteritis in broilers: an updated review on the pathogenesis," *Avian Pathology* 40(4):341-347 (2011).

Vicuña, et al., "Dose titration of FITC-D for optimal measurement of enteric inflammation in broiler chicks," *Poultry Science* 94:1353-1359 (Accepted Feb. 2015).

Williams, "Intercurrent coccidiosis and necrotic enteritis of chickens: rational, integrated disease management by maintenance of gut integrity," *Avian Pathology* 34(3):159-180 (2005).

Xie, et al., "Changes in Serum Ovotransferrin Levels in Chickens with Experimentally Induced Inflammation and Diseases," *Avian Dis* 46(1):122-131 (2002).

U.S. Appl. No. 15/555,531, filed Sep. 4, 2017, US 2018-0312905, Nov. 1, 2018, Igwe.

U.S. Appl. No. 16/612,398, filed Nov. 10, 2019, Flügel.

U.S. Appl. No. 16/977,023, filed Aug. 31, 2020, Flügel.

Carozzi, et al., "Fecal Collection and Stabilization Methods for Improved Fecal DNA Test for Colorectal Cancer in a Screening Setting," *Journal of Cancer Research* vol. 2013, Article ID 818675 8 pages (2013).

Giansanti, et al., "Physiological roles of ovotransferrin," *Biochim Biophys Acta* 1820(3):218-225 (Mar. 2012).

Helle, et al., "Transferrin-Ovotransferrin," Avian Immunology (Second Edition), (2014) ; https://www.sciencedirect.com/topics/biochemistry-genetics-and-molecular-biology/ovotransferrin.

Howard, et al., "Urinary albumin, transferrin and iron excretion in diabetic patients," *Kidney International* 40(5):923-926 (1991).

Jochen, "What is bird poop?" (2011). https://www.10000birds.com/what-is-bird-poop.htm.

Miller, et al., "Bacteriophage therapy for control of necrotic enteritis of broiler chickens experimentally infected with Clostridium perfringens," *Avian Diseases* 54(1):33-40 (2010).

Rath, et al., "Serum ovotransferrin as a biomarker of inflammatory diseases in chickens," *Poultry Science* 88(10):2069-2074 (Oct. 2009).

Trung, et al., "Non-Typhoidal Salmonella Colonization in Chickens and Humans in thr Mekong Delta of Vietnam," *Zoonoses Public Health* 64(2):94-99 (Mar. 2017).

Amendment & Response filed Aug. 19, 2022, for copending U.S. Appl. No. 16/612,398.

Final Office Action dated Oct. 6, 2022, for copending U.S. Appl. No. 16/612,398.

Interview Summary dated Dec. 7, 2022, for copending U.S. Appl. No. 16/612,398.

Notice of Allowance dated Dec. 19, 2022, for copending U.S. Appl. No. 16/612,398.

Office Action dated Nov. 23, 2022, for copending U.S. Appl. No. 16/977,023.

Agunos, et al., "A Systematic Review Characterizing On-Farm Sources of *Campylobacter* spp. For Broiler Chickens," *Plos One* 9(8):e104905 (Aug. 2014).

Dallal, et al., "Prevalence and antimicrobial resistance profiles of *Salmonella* serotypes, *Campylobacter* and *Yersinia* spp. Isolated from retail chicken and beef, Tehran, Iran," *Food Control* 21:388-392 (2010).

Devriese, et al., "*Pseudomonas aeruginosa* Infection on a Broiler Farm," *Avian Pathology* 4:233-237 (1975).

Ducatelle, et al., "Biomarkers for monitoring intestinal health in poultry: present status and future perspectives," *Vet. Res.* 49:1-9 (May 2018).

Santos, et al., "Pathobiology of *Salmonella*, intestinal microbiota, and the host innate immune response," *Front. Immunol.* 5:1-7 ((May 2014).

Examiner's Answer for copending application U.S. Appl. No. 15/555,531, dated Jul. 30, 2021.

Reply Brief for copending U.S. Appl. No. 15/555,531, filed Sep. 29, 2021.

U.S. Appl. No. 17/413,548, filed Jun. 12, 2021, Pelzer.

Amendment & Response filed Feb. 22, 2023 for copending application U.S. Appl. No. 16/977,023.

Non Final Final Office Action dated Apr. 5, 2023 for copending application U.S. Appl. No. 16/977,023.

Bilder, et al., "Pooled testing procedures for screening high volume clinical specimens in heterogenous populations," *Stat. Med.* 31(27):3261-3268 (Nov. 2012).

Public Health Veterinarian (Ante-mortem inspection 2016); (Sep. 2016).

Amendment & Response filed Jul. 29, 2023 for copending application U.S. Appl. No. 16/977,023.

Final Office Action for copending application U.S. Appl. No. 16/977,023, dated Sep. 21, 2023.

\* cited by examiner

IN VITRO METHOD FOR DETECTING INTESTINAL BARRIER FAILURE IN ANIMALS

CROSS REFERENCE TO RELATED APPLICATIONS

The present application is US national stage of international application PCT/EP2019/054939 which had an international filing date of Feb. 28, 2019, and which was published on Sep. 6, 2019. Priority is claimed to European application 18159632.1, filed on Mar. 2, 2018. The contents of these prior applications is hereby incorporated by reference in their entirety.

FIELD OF THE INVENTION

The present invention relates to an in vitro method for detecting intestinal barrier failure in animals. More specifically, the present invention pertains to an acute phase protein (APP)-based method for evaluating the gut health status of an individual animal and of an animal population, respectively.

BACKGROUND OF THE INVENTION

Intestinal health is critically important for the welfare and performance of livestock animals. Enteric diseases that affect the structural integrity of the gastrointestinal tract (GIT) lead to high economic losses due to reduced weight gain, poor feed conversion efficiency, increased mortality rates and greater medication costs (M'Sadeq, S. A., Wu, S., Swick, R. A. & Choct, M. (2015). Towards the control of necrotic enteritis in broiler chickens with in-feed antibiotics phasing-out worldwide. *Animal Nutrition*, 1, 1-11; Timbermont, L., Haesebrouck, F., Ducatelle, R. & Van Immerseel, F. (2011). Necrotic enteritis in broilers: an updated review on the pathogenesis. *Avian Pathol*, 40, 341-347).

An intact intestinal barrier provides a number of physiological and functional features, including nutrient digestion and absorption, host metabolism and energy generation, a stable microbiome, mucus layer development, barrier function, and mucosal immune responses (Kogut, M. H. and R. J. Arsenault (2016). Editorial: Gut health: The new paradigm in food animal production. Frontiers in Veterinary Science 3 (AUG)). As the largest organ in the body, the gut serves as a selective barrier to take up nutrients and fluids into the body, while excluding undesirable molecules and pathogens. Therefore, proper gut barrier function is essential to maintain optimal health and balance throughout the body, and represents a key line of defense against foreign antigens from the environment.

Coccidiosis and necrotic enteritis (NE) probably are the most common enteric diseases of poultry (Dalloul, R. A. & Lillehoj, H. S. (2006). Poultry coccidiosis: recent advancements in control measures and vaccine development. *Expert Rev Vaccines*, 5, 143-163; Williams, R. B. (2005). Intercurrent coccidiosis and necrotic enteritis of chickens: rational, integrated disease management by maintenance of gut integrity. *Avian Pathol*, 34, 159-180). In poultry, coccidiosis can be caused by multiple species belonging to the genus *Eimeria*, from which *Eimeria acervulina*, *E. maxima* and *E. tenella* are the most common species in intensively reared broilers. Depending on the species, the lesions can range from a limited malabsorptive enteritis (*E. acervulina*) to more severe inflammation of the intestinal wall (*E. maxima*) and even extensive caecal haemorrhage and death (*E. tenella*) (Chapman, H. D. (2014). Milestones in avian coccidiosis research: a review. *Poult Sci*, 93, 501-511). Furthermore, the presence of *Eimeria* species can also exacerbate the outcome of co-infection with bacterial pathogens such as *Clostridium perfringens* (Moore, R. J. (2016). Necrotic enteritis predisposing factors in broiler chickens. *Avian Pathol*, 45, 275-281). Indeed, the mucosal damage caused by these coccidial pathogens is an important predisposing factor for necrotic enteritis. NE is the most common clostridial enteric disease in poultry, which typically occurs in broiler chickens. The disease is caused by *C. perfringens* and can occur either as an acute clinical or as a mild subclinical form. Acute NE typically leads to a massive increase in flock mortality. The more common subclinical form is characterized by multifocal necrosis and inflammation of the small intestine with a significant decline in growth performance. The reduction in performance is not only associated with impaired growth rate and feed conversion during production, but also with increased condemnation rates in broilers due to hepatitis at processing (Paiva, D. & McElroy, A. (2014). Necrotic enteritis: Applications for the poultry industry. *Journal of Applied Poultry Research*, 23, 557-566). Both coccidiosis and necrotic enteritis can be present in a flock without showing clinical signs. Therefore, multiple birds have to be sacrificed for macroscopic examination of the intestine to diagnose the disease.

Similar considerations apply for other enteric diseases or conditions in livestock animals which are leading to mucosal damage, such as severe bacterial overgrowth in the small intestine, all forms of excessive gut inflammation, exposure to mycotoxins, and every condition which leads to intestinal barrier failure. In addition, intestinal barrier failure might enable normal inhabitants of the GIT, like *Enterococcus caecorum* to invade the systemic circulation. This can lead to further diseases like arthritis and osteomyelitis and finally lead to lower performance of the animals or the animal flock, respectively.

A marker, or a set of markers, that can accurately detect intestinal barrier failure or intestinal inflammation and concomitant perturbation of the intestinal integrity at an early stage would thus be highly desirable.

Recently, there has been increased interest in research on intestinal permeability in chickens, resulting in different strategies to measure intestinal inflammation and concomitant intestinal barrier failure. However, none of the proposed strategies represent a good marker for the broiler industry as they are either not applicable under field conditions (e.g. oral administration of a marker that can be measured in the blood on a later timepoint (Gilani, S., Howarth, G. S., Kitessa, S. M., Tran, C. D., Forder, R. E. A. & Hughes, R. J. (2017). New biomarkers for increased intestinal permeability induced by dextran sodium sulphate and fasting in chickens. *J Anim Physiol Anim Nutr (Berl)*, 101, e237-e245; Vicuna, E. A., Kuttappan, V. A., Tellez, G., Hernandez-Velasco, X., Seeber-Galarza, R., Latorre, J. D., et al. (2015). Dose titration of FITC-D for optimal measurement of enteric inflammation in broiler chicks. *Poult Sci*, 94, 1353-1359) or non-specific for intestinal barrier failure, such as serum markers that can be elevated by non-gastrointestinal conditions as well (Chen, J., Tellez, G., Richards, J. D. & Escobar, J. (2015). Identification of Potential Biomarkers for Gut Barrier Failure in Broiler Chickens. *Front Vet Sci*, 2, 14; O'Reilly, E. L. & Eckersall, P. D. (2014). Acute phase proteins: a review of their function, behaviour and measurement in chickens. *Worlds Poultry Science Journal*, 70, 27-43; Xie, H., Newberry, L., Clark, F. D., Huff, W. E., Huff, G. R., Balog, J. M., et al. (2002). Changes in serum ovotransferrin levels in chickens with experimentally induced inflammation and diseases. *Avian Dis*, 46, 122-131).

It was thus a remaining need to provide a fast and reliable, ideally non-invasive ante mortem method for determining whether or not an individual animal or an animal population, and in particular an avian population suffers from intestinal barrier failure that can be performed under field conditions at low cost and with minimal effort.

SUMMARY OF THE INVENTION

Accordingly, one objective of the present invention is to provide an in vitro method for detecting intestinal barrier failure in an avian population, the method comprising the following steps:
   a) collecting a pooled fecal sample deriving from an avian population and
   b) determining the amount of at least one protein marker contained in said sample;
wherein
the at least one protein marker comprises or consists of an acute phase protein or a functional fragment thereof,
and wherein
an increased amount of said at least one protein marker contained in said sample versus a reference sample indicates intestinal barrier failure.

An additional aspect of the present application is the use of acute phase proteins or functional fragments thereof, as fecal markers for detecting intestinal barrier failure in an avian population.

A further objective of the present invention is the provision of an in vitro method for detecting the extent of intestinal barrier failure in an avian flock, the method comprising the following steps:
   a) collecting a pooled fecal sample deriving from an avian flock;
   b) determining the amount of at least one protein marker contained in the sample material;
wherein
the at least one protein marker comprises or consists of an acute phase protein or a functional fragment thereof,
and wherein
the amount of said at least one protein marker contained in the sample indicates the extent of the intestinal barrier failure.

Finally, the present invention provides an in vitro method for monitoring the status of the intestinal barrier in an avian flock, the method comprising the following steps:
   a) collecting a pooled fecal sample deriving from an avian flock at consecutive points in time;
   b) determining the amount of at least one protein marker contained in the samples obtained in step a); and
   c) determining deviations in the amounts of said at least one protein marker contained in the samples obtained in step a);
wherein
the at least one protein marker comprises or consists of an acute phase protein or a functional fragment thereof.

In the following, the crucial aspects of the present invention are described in detail.

DETAILED DESCRIPTION OF THE INVENTION

The present inventors have unexpectedly found that the amount of acute phase protein (APP)-based markers contained in sample material of animal origin correlates with the manifestation of intestinal barrier failure. More specifically, it was found that the amount of these APP-based markers contained in a pooled fecal sample deriving from an avian population correlates with the manifestation of intestinal barrier failure in said avian population.

In the context of the present invention, the term "APP-based marker" refers either to proteins comprising or consisting of an APP; or to polypeptides/proteins comprising or consisting of functional fragments of an APP.

More specifically, the inventors have found that an increase in the amount of the APP-based marker contained in intestinal sample material of animal origin versus a reference sample indicates intestinal barrier failure.

Accordingly, the present invention pertains to an in vitro method for detecting intestinal barrier failure in animals, the method comprising the following steps:
   a) collecting intestinal sample material of an individual animal or of an animal population; and
   b) determining the amount of at least one protein marker contained in said sample material;
wherein
the at least one protein marker comprises or consists of an acute phase protein or a functional fragment thereof,
and wherein
an increased amount of said at least one protein marker contained in said sample versus a reference sample indicates intestinal barrier failure.

Further, the present invention provides an in vitro method for detecting intestinal barrier failure in an avian population, the method comprising the following steps:
   a) collecting a pooled fecal sample deriving from an avian population and
   b) determining the amount of at least one protein marker contained in said sample;
wherein
the at least one protein marker comprises or consists of an acute phase protein or a functional fragment thereof,
and wherein
an increased amount of said at least one protein marker contained in said sample versus a reference sample indicates intestinal barrier failure.

As used in the context of the present invention, the term "intestinal barrier failure" refers to conditions in which the intestinal barrier function is significantly impaired (e.g. due to oxidative stress, poorly digestible protein, coccidiosis, etc.); and comprises conditions of intestinal barrier dysfunction, intestinal leakages/permeability and conditions caused by histopathologic injuries. Intestinal barrier failure is often associated with inflammatory processes. The terms "intestinal barrier failure" and "gut barrier failure" may be used interchangeably.

As indicated in the above, the at least one protein marker comprises or consists of an acute phase protein or a functional fragment thereof. Acute phase proteins (APPs) are known in the art.

In one embodiment of the present invention, the aforementioned method is applied using only one specific protein marker. Alternatively and also in accordance with the present invention, two or more protein markers may be analyzed simultaneously.

Suitable protein markers to be used in the method of the present invention are, for example, transferrin/ovotransferrin (OTF), haptoglobin (HAPT, avian: PIT54), C-reactive protein (CRP), ceruloplasmin, fibrinogen, mannan binding lectin, serum amyloid A (SAA), long chain pentraxin PTX3, a1 acid glycoprotein (AGP).

For example, ovotransferrin (OTF) and/or long chain pentraxin PTX3 may be used as marker for intestinal barrier failure in avians.

As an alternative, functional fragments of the above proteins may be used as protein markers. The term "fragment" refers to a polypeptide or protein derivative of a specific protein having a decreased amino acid chain length. The fragments according to the present invention have epitopes that can be identified specifically be antibodies.

In one embodiment, the at least one protein marker is ovotransferrin or a functional fragment thereof.

The reference sample is a species-specific control representing an intact intestinal barrier or gut barrier. Suitable reference samples are samples obtained from an individual animal or from an animal population of the same animal species or sub-species, whereby said animal or said animal population has a proven intact intestinal barrier.

As an example, a reference sample may be taken within an animal trial from an animal of a non-treated control, which was checked via pathology, histopathology and/or other measures to have no signs of intestinal barrier failure.

The protein based markers may be detected and quantified using the commonly known, conventional techniques, such as immunoassays like ELISA (Enzyme-linked Immunosorbent Assay), lateral flow assays, mass spectrometry (MS) analyses, or any method enabling the detection of proteins or functional fragments thereof.

In one specific embodiment, the at least one protein marker is detected and quantified via ELISA.

The use of monoclonal antibodies enables a specific detection in the complex sample matrix used for the analysis.

The method of the present invention may be used for determining whether or not an individual animal suffers from intestinal barrier failure. In that case, the intestinal sample material originates from an individual animal.

The individual animal may for example be a pet or domestic animal, a farm animal as occurring in live stocks, a wild-living animal or a zoo animal. Further, animal individuals being transported for slaughter or for re-location may be examined using the above method.

In one embodiment, the individual animal is an avian subject.

The avian subject to be tested is preferably poultry. Preferred poultry according to the invention are chickens, turkeys, ducks and geese. The poultry can be optimized for producing young stock. This type of poultry is also referred to as parent and grandparent animals. Preferred parent and grandparent animals are, accordingly, (grand)parent broilers, (grand)parent ducks, (grand)parent turkeys and (grand) parent geese.

The poultry according to the invention can also be selected from fancy poultry and wild fowl. Preferred fancy poultry or wild fowl are peacocks, pheasants, partridges, guinea fowl, quails, capercailzies, goose, pigeons and swans. Further preferred poultry according to the invention are ostriches and parrots. Most preferred poultry according to the invention are broilers.

The intestinal sample material obtained from an individual animal may be selected from the group consisting of gut content samples, samples of bodily excrements and solutions or suspensions thereof; and from materials being contaminated with bodily excrements. The term "gut content" is to be understood as the content of the small intestine, the content of the large intestine and/or the content of the caecum. Methods for taking such gut content samples are known in the art.

As used in the context of the present invention, bodily excrements are fecal or cecal excrements. Materials being contaminated with bodily excrements are, for example, dust samples, swab samples, litter samples, liquid manure samples, fur samples, feather samples and skin samples.

In general, the term "litter" is to be understood as a mixture of animal excrements with the bedding material.

As used in the context of this embodiment, the term "litter samples" refers to excremental droppings from an individual animal. Further, in the context this embodiment, the term "liquid manure samples" refers to an excremental sample containing feces and urine from an individual animal.

Samples from individual animals can be taken either directly from the animal, e.g. with swabs. Alternatively and especially in case of single-housed animals, the sample material can be collected from the floor of the pen, cage or slat. The sample material has to be assignable to the investigated animal.

In one embodiment, the intestinal sample material used for determining whether or not an individual animal suffers from intestinal barrier failure is feces.

For specific applications, it is also useful to analyze gut content samples, e.g. samples from the small intestine, samples from the large intestine and/or samples from the caecum.

Suitable sample volumes are, for example, 0.05 ml to 20 ml or 0.1 to 20 ml, in particular 0.2 to 10 ml, preferably 0.5 to 5 ml. Suitable sample masses are, for example 0.05 g to 20 g or 0.1 to 20 g, in particular 0.2 to 10 g, preferably 0.5 to 5 g In an alternative embodiment, the method is used for determining whether or not an animal population suffers from intestinal barrier failure. In that case, the sample material originates from the group of animals to be tested.

As used herein, the term "animal population" refers to a group of animal individuals belonging to the same species. The animal population may for example be a group of pets or domestic animals as occurring in animal breeding, a group of farm animals as occurring in livestock production or in livestock breeding, or a group of wild-living animals or zoo animals.

In one embodiment, the animal population is an animal flock as occurring in livestock production processes. For example, the animal population or the animal flock can be an avian flock; a flock of sheep, goat or cattle, a flock of horses or a flock of pigs.

In one specific embodiment, the animal population is an avian population.

The animal population preferably is an avian flock. The avian flock according to the invention is preferably poultry. Preferred poultry according to the invention are chickens, turkeys, ducks and geese. The poultry can be optimized for producing young stock. This type of poultry is also referred to as parent and grandparent animals. Preferred parent and grandparent animals are, accordingly, (grand)parent broilers, (grand)parent ducks, (grand)parent turkeys and (grand) parent geese.

The poultry according to the invention can also be selected from fancy poultry and wild fowl. Preferred fancy poultry or wild fowl are peacocks, pheasants, partridges, guinea fowl, quails, capercailzies, goose, pigeons and swans. Further preferred poultry according to the invention are ostriches and parrots. Most preferred poultry according to the invention are broilers.

The method of the present invention is particularly suitable for determining the health status of an animal population via bulk testing. As used herein, the term "bulk testing"

refers to a test method, wherein the sample material is a pooled sample of an animal population. A "pooled sample" in the context of this embodiment is to be understood as a composite sample from randomly selected separate samples, one sample taken with one or several moistened fabric swabs or pooled samples made up of separate samples of fresh samples taken at random from a number of sites in the house or space in which the animal population or the animal flock is kept. It may be necessary that the sample material is homogenized prior to sample analysis. Suitable homogenization techniques are known in the art.

The pooled samples reflect the amount of APP-based protein markers present in the animal population.

The sample material obtained from an individual animal may be selected from the group consisting of gut content samples, samples of bodily excrements and solutions or suspensions thereof; and from materials being contaminated with bodily excrements. Materials being contaminated with bodily excrements are, for example, dust samples, swab samples, litter samples, liquid manure samples, fur samples, feather samples and skin samples.

As used in the context of this embodiment, the term "litter samples" refers to mixed excremental droppings in the pen, cage or slat. Further, in the context this embodiment, the term "liquid manure samples" refers to mixed excremental samples containing feces and urine.

These litter samples can, for example, be collected from an animal population using the overshoe method or using litter grabs at different places in the pen.

Boot swabs being sufficiently absorptive to soak up moisture are particularly suitable for collecting pooled animal samples. Tube gauze socks are also acceptable.

In case the animal population is kept in cages or slats, the excremental samples may be collected by a conveying belt.

In one embodiment, the sample material used for determining whether or not an animal population suffers from intestinal barrier failure is feces. Preferably, the sample material is a pooled fecal sample deriving from an avian flock.

For specific applications, it is also useful to analyze pooled gut content samples, e.g. pooled samples from the small intestine, pooled samples from the large intestine and/or pooled samples from the caecum.

Suitable sample volumes are, for example, 0.1 to 20 ml, in particular 0.2 to 10 ml, preferably 0.5 to 5 ml. Suitable sample masses are, for example 0.1 to 20 g, in particular 0.2 to 10 g, preferably 0.5 to 5 g.

Depending on the sample material and storage conditions, it may be helpful to stabilize the samples taken in order to avoid enzymatic degradation of the APPs contained in the samples, for example by treating the samples with protease inhibitors. Preferably, the stabilizing agent is added to the sample immediately after sample collection.

In accordance with the above, one specific embodiment of the present application pertains to an in vitro method for detecting intestinal barrier failure in an avian flock, the method comprising the following steps:
 a) collecting and pooling fecal sample material deriving from said avian flock;
 b) optionally stabilizing the pooled sample material; and
 c) determining the amount of ovotransferrin contained in said pooled sample material;
wherein
an increased amount of ovotransferrin contained in the sample versus a reference sample indicates intestinal barrier failure.

In addition to the above, the inventors have unexpectedly found that the amount of a specific APP-based marker contained in intestinal sample material deriving from an individual animal or from an animal population correlates with the extent of intestinal barrier failure. Accordingly, the present invention provides an in vitro method for detecting the extent of intestinal barrier failure in animals, the method comprising the following steps:
 a) collecting intestinal sample material of a specific animal or of an animal population; and
 b) determining the amount of at least one protein marker contained in the sample material;
wherein
the at least one protein marker comprises or consists of an acute phase protein or a functional fragment thereof, and wherein
the amount of said at least one protein marker contained in the sample indicates the extent of the intestinal barrier failure.

Further, the present invention provides an in vitro method for detecting the extent of intestinal barrier failure in an avian flock, the method comprising the following steps:
 a) collecting a pooled fecal sample deriving from an avian flock;
 b) determining the amount of at least one protein marker contained in the sample material;
wherein
the at least one protein marker comprises or consists of an acute phase protein or a functional fragment thereof, and wherein
the amount of said at least one protein marker contained in the sample indicates the extent of the intestinal barrier failure.

Suitable sample materials, protein markers and testing parameters and -conditions are as defined above.

The above method may be carried out using only one specific protein marker. Alternatively and also in accordance with the present invention, two or more protein markers may be analyzed simultaneously.

In a particularly preferred embodiment, the intestinal sample material is a pooled fecal sample deriving from an avian flock and the at least one protein marker is ovotransferrin or a functional fragment thereof.

The present invention provides the abovementioned methods for detecting intestinal barrier failure and for determining the extent thereof, respectively. This enables the farmer to make a qualified decision on whether or not measures for improving intestinal health are to be taken.

Measures against the development and/or against the progression of intestinal barrier failure involve feeding or administering health-promoting substances, such as zootechnical feed additives, or therapeutic agents. The term "administering" or related terms includes oral administration. Oral administration may be via drinking water, oral gavage, aerosol spray or animal feed. The term "zootechnical feed additive" refers to any additive used to affect favorably the performance of animals in good health or used to affect favorably the environment. Examples for zootechnical feed additives are digestibility enhancers, i.e. substances which, when fed to animals, increase the digestibility of the diet, through action on target feed materials; gut flora stabilizers; micro-organisms or other chemically defined substances, which, when fed to animals, have a positive effect on the gut flora; or substances which favorably affect the environment. Preferably, the health-promoting substances are selected from the group consisting of probiotic agents, praebiotic agents, botanicals, organic/fatty acids, zeolithes, bacteriophages and bacteriolytic enzymes or any combinations thereof.

The inventors have found that the testing procedures underlying the present invention may also be used for monitoring the intestinal health status in animals.

As used in the context of this embodiment, the term "intestinal health status" refers to status of the intestinal barrier.

By the above method, the development or the progression of an intestinal barrier failure may be detected. On the other hand, the effectiveness of measures taken against the development and/or against the progression of intestinal barrier failure may be controlled.

Accordingly, the present invention also pertains to an in vitro method for monitoring the intestinal health status in animals, the method comprising the following steps:
 a) collecting intestinal sample material of a specific animal or of an animal population at consecutive points in time;
 b) determining the amount of at least one protein marker contained in the samples obtained in step a); and
 c) determining deviations in the amounts of the at least one protein marker contained in the samples obtained in step a);
wherein
the at least one protein marker comprises or consists of an acute phase protein or a functional fragment thereof.

Further, the present invention provides an in vitro method for monitoring the status of the intestinal barrier in an avian flock, the method comprising the following steps:
 a) collecting a pooled fecal sample deriving from an avian flock at consecutive points in time;
 b) determining the amount of at least one protein marker contained in the samples obtained in step a); and
 c) determining deviations in the amounts of said at least one protein marker contained in the samples obtained in step a);
wherein
the at least one protein marker comprises or consists of an acute phase protein or a functional fragment thereof.

Therein, an increase over time in the amount of said at least one protein marker over time indicates the development or progression of intestinal barrier failure. Conversely, a decrease in the amount of said at least one protein marker over time indicates improvements in the intestinal health situation which may be caused by natural healing processes or by specific measures being taken against the development or progression of intestinal barrier failure.

An "increase" or a "decrease" in the amount of the protein marker typically refers to a statistically relevant amount.

The above method may be carried out using only one specific protein marker. Alternatively and also in accordance with the present invention, two or more protein markers may be analyzed simultaneously.

Suitable sample materials, protein markers and testing parameters and -conditions are as defined above. In a specific embodiment, the intestinal sample material is a pooled sample deriving from an avian flock and the at least one protein marker is ovotransferrin or a functional fragment thereof.

As an example, after initial determination of the amount of said protein marker in an intestinal sample, the amount of said at least one specific biomarker may be monitored in test samples collected and analyzed in a weekly, daily our hourly manner. In one embodiment, excremental samples are collected and analyzed at consecutive days. The excremental test samples may be taken and analyzed on a daily basis from birth to slaughter.

In a specific embodiment for poultry, a first test sample is preferably taken and analyzed during the initial growth phase (starter phase, day 5 to day 10), a second test sample is taken and analyzed during the enhanced growth phase (day 11 to day 18) and, optionally, a third test sample is taken and analyzed on a later stage.

In an alternative embodiment, a first test sample is taken and analyzed in the initial growth phase and further test samples are taken and analyzed for example on a daily basis during the enhanced growth phase, optionally until slaughter.

A further aspect of the present invention is the use of acute phase proteins as intestinal markers for detecting intestinal barrier failure in an animal subject or in an animal population. A specific embodiment of the present invention is the use of ovotransferrin as a fecal marker for detecting intestinal barrier failure in an avian subject or in an avian population.

Applications of the methods according to the invention are for example (i) aiding in the diagnosis and/or prognosis of intestinal barrier failure caused by enteric diseases; (ii) monitoring the progress or reoccurrence of intestinal barrier failure or (iii) aiding in the evaluation of treatment efficacy for an animal population undergoing or contemplating treatment.

Applications of the invention in particular help to avoid loss in animal performance like weight gain and feed conversion.

In the following, the invention is illustrated by non-limiting examples and exemplifying embodiments.

EXAMPLES

Coccidiosis and necrotic enteritis in broiler chickens were used as models for intestinal barrier failure. Ovotransferrin serves as protein marker.

Necrotic Enteritis Trials—Sample Collection

Groups of 27 one-day-old Ross 308 broiler chickens were fed a diet rich in proteins and non-starch polysaccharides which predispose to the development of necrotic enteritis. The detailed diet composition was described by Gholamiandehkordi et al. (Gholamiandehkordi, A. R., Timbermont, L., Lanckriet, A., Van Den Broeck, W., Pedersen, K., Dewulf, J., et al. (2007). Quantification of gut lesions in a subclinical necrotic enteritis model. *Avian Pathol*, 36, 375-382). Other predisposing factors consist of the administration of Gumboro vaccine to induce mild immunosuppression and a ten-fold dose of coccidiosis vaccine (either Paracox-8 or Hipracox, depending on the trial) to induce predisposing intestinal damage. To induce necrotic lesions, animals were challenged with approximately $4.10^8$ CFU of the netB-positive *C. perfringens* strain CP56 on three consecutive days, after which the animals were euthanized. At necropsy, lesion scoring in the small intestine (duodenum, jejunum and ileum) was performed as described by Keyburn et al. (Keyburn, A. L., Sheedy, S. A., Ford, M. E., Williamson, M. M., Awad, M. M., Rood, J. I., et al. (2006). Alpha-toxin of *Clostridium perfringens* is not an essential virulence factor in necrotic enteritis in chickens. *Infect Immun*, 74, 6496-6500) as follows: score 0=no lesions, score 1=congested intestinal mucosa, score 2=focal necrosis or ulcerations (1-5 foci), score 3=focal necrosis or ulcerations (6-15 foci), score 4=focal necrosis or ulcerations (≥16 foci), score 5=patches of necrosis of 2-3 cm long, score 6=diffuse necrosis. Birds with a lesion score of 2 or more are classified as necrotic enteritis positive. Fresh cloacal samples were collected from all birds and frozen at −70° C. In addition, mixed litter was collected from each pen and frozen at −70° C.

After lesion scoring, the samples were grouped according to the disease severity of the animal, leading to the following disease severity groups: birds that received all predisposing factors but were not challenged with *C. perfringens*: negative control; birds challenged with *C. perfringens* but no necrosis: score 0 or challenged with *C. perfringens* and various severity degrees: score 2 (mild), score 3-4 (moderate) or score 5-6 (severe).

Coccidiosis Trials—Sample Collection

Fifteen-day-old Ross 308 broiler chicks were orally challenged with *E. acervulina* and *E. tenella*. One mixed litter sample from each pen and cloacal samples from all birds were collected 7 days after challenge, when the chickens were euthanized for lesion scoring using the method of Johnson and Reid (Johnson, J. & Reid, W. M. (1970). Anticoccidial drugs: lesion scoring techniques in battery and floor-pen experiments with chickens. *Exp Parasitol*, 28, 30-36). On the same day, mixed litter and cloacal content samples were collected from their age-matched controls. All challenged birds showed macroscopically visible lesions of *Eimeria* infection, with a mean coccidiosis score of 5.11±0.51, whereas only one out of then birds in the unchallenged control group was coccidiosis positive (coccidiosis score=1). All samples were stored at −70° C.

Ovotransferrin Detection by Enyzme-Linked Immunosorbent Assay (ELISA)

Eight samples from the negative control birds (not challenged with *C. perfringens*) and eight sample per necrosis score group from challenged birds were selected. Also litter samples collected at the day of necropsy were included (one litter samples per pen, with in total 3 samples from pens with non-challenged birds and 3 samples from pens with challenged birds). Additionally, the ovotransferrin concentration was determined in both cloacal samples and litter samples from the coccidiosis trial. Therefore, 1 litter sample per pen was used, with in total 5 samples from pens with non-challenged birds and 6 samples from pens with *Eimeria*-challenged birds. Additionally, 20 cloacal samples from either *Eimeria*-challenged birds (n=10) or their non-challenged controls (n=10) were selected.

Unprocessed cloacal material or homogenized litter material was thawed at room temperature. 150 mg cloacal content or litter material was diluted in 1500 µl TBS (50 mM Tris, 150 mM NaCl, pH=7.2) with protease inhibitor cocktail (P2714, Sigma-Aldrich). The samples were mixed by vortex (2×1 min). Proteins (supernatants) were collected after centrifugation (13.000× g, 10', 4° C.) and were used in duplicate (1/50 dilution) in the ELISA (Chicken Ovotransferrin ELISA, KT-530, Kamiya Biomedical Company, Tukwila, USA). The ELISA was performed according to the instructions of the manufacturer.

Statistical Analysis

Normality of the data was tested with the D'Agostino-Pearson normality test.

Differences in ovotransferrin levels between necrotic enteritis severity groups (as measured by ELISA) were calculated using an a Kruskal-Wallis test, followed by a Dunn's post test.

Differences in ovotransferrin levels between the *Eimeria*-challenged and the non-challenged control group were calculated using a Mann-Whitney test.

The Spearman rank correlation was used to assess the relationship between the ovotransferrin concentration in the cloacal samples and either the necrotic enteritis lesion score or the coccidiosis score. Results were reported as means and standard error of the means (SEM).

Correlation of Fecal Ovotransferrin Concentration with Severity of Necrotic Enteritis Most samples from birds suffering from either mild necrotic enteritis (score 2) or without intestinal lesions (both challenged and negative control animals) showed a low signal. In samples from birds with more severe necrotic enteritis (necrosis score 3), significantly more ovotransferrin was detected than in samples from challenged birds who did not show intestinal disease (score 0), see Table 1. Furthermore, there was a positive correlation between the necrotic enteritis disease severity and the ovotransferrin concentration in the fecal samples from the NE in vivo trial ($p=0.0004$).

Table 1 represents the ovotransferrin concentration (mean ± standard error of the means) in faeces from birds that received all predisposing factors but were not challenged with *C. perfringens* (neg. ctr; n = 8) or from birds challenged with *C. perfringens* resulting in varying degrees of necrotic enteritis: no necrotic lesions (score 0; n = 8); mild intestinal necrosis (score 2; n = 8); moderate necrotic enteritis (score 3-4; n = 8) or severe necrosis (score 5-6; n = 8). * $p < 0.05$.

|  | neg. ctr (BHI) [µg/g] | Score 0 [µg/g] | Score 2 [µg/g] | Score 3-4 [µg/g] | Score 5-6 [µg/g] |
| --- | --- | --- | --- | --- | --- |
| Mean | 1.80 | 1.01 | 1.16 | 3.59 | 5.87 |
| Std. Error | 0.4353 | 0.2605 | 0.1921 | 1.034 | 1.504 |

Correlation of Fecal Ovotransferrin Concentration with Severity of Coccidiose

Birds challenged with *E. acervulina* and *E. tenella* were used as a second model for intestinal barrier failure. The ovotransferrin levels in samples from coccidiosis-positive birds were elevated as compared to the unchallenged controls ($p=0.0029$). Furthermore, there was a positive correlation between the coccidiosis score and the ovotransferrin concentration in the faeces ($p=0.0082$). This difference in ovotransferrin levels was also reflected in the litter samples, where significantly higher ovotransferrin levels were detected in litter from *Eimeria*-challenged birds than in litter samples from non-challenged control groups ($p=0.0043$), see Table 2.

Table 2 represents the ovotransferrin concentration (mean ± standard error of the means) in faeces (grey) or mixed litter (white) from experimental coccidiosis-infected birds (coccidiosis; individual faeces samples: n = 10 or mixed litter samples: n = 6) or non-challenged control birds (neg. ctr; individual faeces: n = 10 or mixed litter samples: n = 5). Significant differences between the coccidiosis-positive group and the non-challenged control group are indicated with ** $p < 0.01$.

|  | neg. ctr | | coccidiosis | |
| --- | --- | --- | --- | --- |
|  | Feces [µg/g] | Litter [µg/g] | Feces [µg/g] | Litter [µg/g] |
| Mean | 4.49 | 1.51 | 24.76 | 24.46 |
| Std. Error | 1.48 | 0.33 | 9.56 | 6.49 |

Results

As shown in the above, elevated fecal ovotransferrin levels were measured in birds with either experimental coccidiosis or necrotic enteritis, which both cause intestinal barrier failure, using different approaches. ELISA analysis samples from different NE in vivo trials revealed that ovotransferrin was more abundant in samples from birds suffering from necrotic enteritis as compared to unchallenged birds. Additionally, elevated ovotransferrin concentrations were measured in samples from cocciciosis-positive birds as compared to their unchallenged controls.

Fecal ovotransferrin levels were significantly correlated with the severity of intestinal barrier failure caused by either coccidiosis or necrotic enteritis.

The degree of gut barrier failure might be classified depending on the severity of the symptom on the affected sites (e.g. necrosis due to *C. perfringens*-induced necrotic enteritis), and the extent of the affected surface area. The degree of gut barrier failure is more severe with NE as this is associated with necrosis, the extent (in terms of surface area) is higher with coccidiosis.

As shown by the above experiments, the measurement of an specific APP (ovotransferrin) is a valuable tool to measure inflammation and concomitant intestinal barrier failure, as it can provide information on specific biological disease processes and is a useful tool to assess efficacy of molecules that reduce gastrointestinal disturbances.

The invention claimed is:

1. An in vitro method for detecting and treating intestinal barrier failure in an avian population, the method comprising:
   a) detecting intestinal barrier failure by the following steps:
      i) collecting a pooled fecal sample derived from the avian population; and
      ii) determining the amount of at least one protein marker contained in said sample; wherein:
         the at least one protein marker comprises an acute phase protein or a functional fragment thereof; and
         an increased amount of said at least one protein marker contained in said sample versus a reference sample indicates intestinal barrier failure; and,
   b) treating the avian population that in step a) has been found to have intestinal barrier failure by administering a zootechnical feed additive; wherein the zootechnical feed additive comprises a digestibility enhancer, a gut flora stabilizer; a probiotic agent; a praebiotic agent, a botanical, an organic acid, a fatty acid, a zeolithe, a bacteriophage, a bacteriolytic enzyme or any combination thereof;
   and wherein the acute phase protein is selected from the group consisting of: ovotransferrin (OTF); haptoglobin (HAPT or PIT54); C-reactive protein (CRP); ceruloplasmin; fibrinogen; mannan binding lectin; serum amyloid A (SAA); long chain pentraxin (PTX3); and a1 acid glycoprotein (AGP).

2. The method of claim 1, wherein the acute phase protein is ovotransferrin.

3. The method of claim 1, wherein the reference sample is a species-specific control representing an intact intestinal barrier.

4. The method of claim 3, wherein the acute phase protein is ovotransferrin.

5. The method of claim 1, wherein the acute phase protein is detected and quantified via an Enzyme-linked Immunosorbent Assay (ELISA).

6. The method of claim 1, wherein the acute phase protein is detected and quantified via a lateral flow assay.

7. The method of claim 1, wherein the pooled fecal sample is stabilized immediately after sample collection.

8. The method of claim 1, wherein the pooled fecal sample is treated with protease inhibitors.

9. The method of claim 3, wherein the acute phase protein is detected and quantified via an Enzyme-linked Immunosorbent Assay (ELISA) or a lateral flow assay.

10. The method of claim 9, wherein the acute phase protein is ovotransferrin.

11. The method of claim 9, wherein the pooled fecal sample is stabilized immediately after sample collection.

12. The method of claim 9, wherein the pooled fecal sample is treated with protease inhibitors.

13. An in vitro method for detecting the extent of intestinal barrier failure in an avian flock, and treating the avian flock for intestinal barrier failure, the method comprising:
    a) detecting the extent of intestinal barrier failure in an avian flock by:
       i) collecting a pooled fecal sample derived from the avian flock; and
       ii) determining the amount of at least one protein marker contained in the sample material; wherein:
          the at least one protein marker comprises an acute phase protein or a functional fragment thereof; and
          the amount of said at least one protein marker contained in the sample indicates the extent of the intestinal barrier failure;
    b) treating the avian population that in step a) has been found to have intestinal barrier failure by administering a zootechnical feed additive; wherein the zootechnical feed additive comprises a digestibility enhancer; a gut flora stabilizer; a probiotic agent; a praebiotic agent; a botanical; an organic acid; a fatty acid; a zeolithe; a bacteriophage; a bacteriolytic enzyme or any combination thereof;
    and wherein the acute phase protein is selected from the group consisting of: ovotransferrin (OTF); haptoglobin (HAPT or PIT54); C-reactive protein (CRP); ceruloplasmin; fibrinogen; mannan binding lectin; serum amyloid A (SAA); long chain pentraxin (PTX3); and a1 acid glycoprotein (AGP).

14. The method of claim 13, wherein the acute phase protein is ovotransferrin.

15. An in vitro method for monitoring the status of the intestinal barrier in an avian flock, the method comprising collecting a pooled fecal sample derived from an avian flock at consecutive points in time; and performing the in vitro method for detecting and treating intestinal barrier failure of claim 1.

16. The method of claim 15, wherein the acute phase protein is ovotransferrin.

17. The method of claim 15, wherein: a) the acute phase protein is ovotransferrin, and b) the reference sample is a species-specific control representing an intact intestinal barrier.

* * * * *